United States Patent
Ranzoni et al.

(10) Patent No.: US 10,036,729 B2
(45) Date of Patent: *Jul. 31, 2018

(54) DETECTION OF CLUSTERS OF MAGNETIC PARTICLES

(75) Inventors: Andrea Ranzoni, Eindhoven (NL); Menno Willem Jose Prins, Rosmalen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1122 days.

This patent is subject to a terminal disclaimer.

(21) Appl. No.: 14/125,618

(22) PCT Filed: Jun. 18, 2012

(86) PCT No.: PCT/IB2012/053051
§ 371 (c)(1),
(2), (4) Date: Dec. 12, 2013

(87) PCT Pub. No.: WO2013/001400
PCT Pub. Date: Jan. 3, 2013

(65) Prior Publication Data
US 2014/0120632 A1    May 1, 2014

(30) Foreign Application Priority Data
Jun. 30, 2011 (EP) .................. 11172070

(51) Int. Cl.
*G01N 33/553* (2006.01)
*G01N 27/74* (2006.01)
*G01N 21/17* (2006.01)
*G01N 21/51* (2006.01)

(52) U.S. Cl.
CPC ....... *G01N 27/745* (2013.01); *G01N 21/1717* (2013.01); *G01N 21/51* (2013.01); *G01N 2021/1727* (2013.01); *G01N 2446/00* (2013.01)

(58) Field of Classification Search
CPC .. G01N 27/745; G01N 21/1717; G01N 21/51; G01N 2021/1727
USPC ........................................... 436/526
See application file for complete search history.

(56) References Cited

U.S. PATENT DOCUMENTS

| 4,725,140 A | 2/1988 | Musha |
| 5,252,493 A | 10/1993 | Fujiwara et al. |
| 2005/0106758 A1 | 5/2005 | Fukumoto et al. |
| 2008/0220411 A1* | 9/2008 | McNaughton ... G01N 33/54313 435/5 |
| 2010/0033158 A1* | 2/2010 | Dittmer .................. B82Y 25/00 324/71.1 |
| 2010/0188076 A1 | 7/2010 | Henricus et al. |
| 2010/0277160 A1 | 11/2010 | Theije et al. |
| 2010/0324828 A1 | 12/2010 | Henricus et al. |
| 2012/0251392 A1 | 10/2012 | Sandhu |

FOREIGN PATENT DOCUMENTS

| JP | 4242167 A | 8/1992 |
| WO | 2005111615 A1 | 11/2005 |
| WO | 2007120095 A1 | 10/2007 |
| WO | 2008001263 A2 | 1/2008 |
| WO | 2010026551 A1 | 3/2010 |
| WO | 2010084383 A1 | 7/2010 |

OTHER PUBLICATIONS

Baudry, J. et al. "Acceleration of the recognition rate between grafted ligands and receptors with magnetic forces". Proceedings of the National Academy of Sciences, 2006, vol. 103, No. 44, pp. 16076-16078.
Rauecker, P. et al: "Schulerversuche zu Magnetismus", Schulversuchspraktikum Physik, Feb. 8, 2001, pp. 1-17.
Ranzoni, A. et al: "Magnetically controlled rotation and torque of uniaxial microactuators for lab-on-a-chip applications", Lab on a Chip, vol. 10, No. 1, Jan. 1, 2010, pp. 179-188.

* cited by examiner

*Primary Examiner* — Chris L Chin

(57) ABSTRACT

The invention relates to a method and a sensor device (100) for the detection of clusters (C) of magnetic particles (MP) in a sample volume (111), particularly of clusters (C) consisting of two magnetic particles (MP) with different binding sites that are bound to a target molecule in a sandwich configuration. Output light (L2) originating from an interaction of input light (L1) with clusters (C) of magnetic particles (MP) is detected. Moreover, the magnetic particles (MP, C) are actuated by a magnetic actuation field (B), wherein said actuation is at least once interrupted by a pause. In this way a high output signal can be achieved that properly reflects the amount of specifically bound clusters (C).

12 Claims, 3 Drawing Sheets

DETECTION OF CLUSTERS OF MAGNETIC PARTICLES

CROSS-REFERENCE TO PRIOR APPLICATIONS

This application is the U.S. National Phase application under 35 U.S.C. § 371 of International Application Serial No. PCT/IB2012/053051, filed on Jun. 18, 2012, which claims the benefit of Application Serial No. EP11172070.2, filed on Jun. 30, 2011. These applications are hereby incorporated by reference herein.

FIELD OF THE INVENTION

The invention relates to a method and a sensor device for the detection of clusters of magnetic particles in a sample volume, wherein said clusters are actuated during the detection by magnetic fields.

BACKGROUND OF THE INVENTION

The WO 2007/120095 A1 discloses a sensor device with which the agglomeration of magnetic particles can be observed by determining their Brownian relaxation time in a carrier fluid. In order to avoid a time-consuming frequency sweep of the required magnetic excitation fields, it is proposed to use pulsed magnetic excitation fields. The described measurements are however complex and difficult to realize.

SUMMARY OF THE INVENTION

It is an object of the invention to provide means that allow for a reliable detection of clusters of magnetic particles in a comparatively simple and robust procedure.

This object is achieved by a method according to claim 1, a sensor device according to claim 2, and a use according to claim 10. Preferred embodiments are disclosed in the dependent claims.

The method according to the present invention serves for the detection of clusters of magnetic particles in a sample volume. In this context, the term "magnetic particle" shall comprise both permanently magnetic particles as well as magnetizable particles, for example superparamagnetic beads. The size of the magnetic particles typically ranges between 3 nm and 50 µm. The "clusters" are agglomerates of two or more magnetic particles which are coupled by some kind of binding. Of particular interest are here chemical bindings (in contrast to bindings that are merely caused by magnetic attraction forces between magnetized particles), in particular specific bindings via special chemical groups and/or intermediate components of interest. The method comprises the following steps:

a) The irradiation of the sample volume with input light. Preferably, this input light is directed into the sample volume as a collimated and/or focused light beam.

b) The actuation of magnetic particles (i.e. single magnetic particles and/or clusters of magnetic particles) in the sample volume by a magnetic actuation field. By definition, the "actuation" comprises the generation of mechanical effects, particularly the exertion of forces on the magnetic particles and/or the movement of magnetic particles. According to the invention, said actuation shall at least once be interrupted by a pause. This means that there is at least one time interval (of non-zero length) during which the magnetic actuation field is zero or at least so small that the magnetic particles are not (in a detectable way) actuated.

c) The detection of output light that originates from an interaction of the above-mentioned input light with clusters of magnetic particles in the sample volume. Due to the interaction with the clusters, certain characteristics (e.g. amount, color, direction etc.) of the output light will depend on the presence (and typically also the amount) of clusters; the detected output light will therefore allow to draw conclusions about the presence/amount of clusters in the sample volume, which is the actual aim of the method.

According to a second aspect, the invention relates to a sensor device for the detection of clusters of magnetic particles in a sample, particularly according to a method of the kind described above. The sensor device comprises the following components:

a) A sample container with a sample volume in which a sample with magnetic particles can be provided. The sample container may for example be realized as a disposable cartridge made from plastic by injection molding.

b) A light source for emitting input light into the sample volume. The light source may for example be a laser diode or an LED.

c) A magnetic field generator, comprising for example a permanent magnet or an electromagnet, for generating a magnetic actuation field that actuates magnetic particles in the sample volume.

d) A control unit for controlling the magnetic field generator such that the actuation of the clusters is at least once interrupted by a pause. The control unit may be realized in dedicated electronic hardware, digital data processing hardware with associated software, or a mixture of both.

e) A light detector for detecting output light that originates from an interaction of the input light with clusters of magnetic particles in the sample volume. The light detector may for example comprise photodiodes, photo resistors, photocells, a CCD chip, or a photo multiplier tube.

The method and the sensor device of the invention allow the robust and accurate detection of clusters of magnetic particles. This is firstly achieved by an optical measurement in which the interaction of clusters with input light is observed. Secondly, it is an important aspect of the invention that the magnetic particles (including the clusters) are actuated by the magnetic actuation field. When this actuation takes place during the detection of output light, it is possible to differentiate between components of the output light originating from clusters of interest and components of the output light originating from other sources. A third important feature of the present invention is that the magnetic actuation is interrupted by at least one pause. This measure seems to be paradox because the aforementioned positive effects of the magnetic actuation on the observation of the output light cannot be achieved during such times of pause. Experiments show however that the sensitivity and accuracy of the detection can be significantly increased if the magnetic actuation is not continuous but interrupted.

In the following, various preferred embodiments of the invention will be described that relate both to the method and the sensor device described above.

The number of pauses by which the magnetic actuation should be interrupted and/or the duration of a pause (as well as other related parameters) are preferably determined from calibration measurements. This means that a plurality of experiments are conducted with a sample of known composition, wherein the number and/or duration (or other parameters) of the pauses is varied in each experiment; the experiment that yields the best results with respect to a given criterion (e.g. the highest output signal which indicates the presence of the clusters of interest) will then indicate the optimal choice for the number and/or duration of the pause(s).

In many practically important examples, an appropriate duration of the pause ranges between about 0.1 second and about 10 seconds, preferably between about 0.5 s and about 5 s, most preferably between about 1 second and about 2 seconds. These values are for instance suited if magnetic particles with a diameter of about 500 nm are used.

A preferred number of interruptions (pauses) of the magnetic actuation field ranges between about 10 and about 50.

The intervals during which the magnetic field is active ("on") preferably have a duration between about 0.1 and 10 s (yielding typical duty cycles between 0.01 and 100).

According to another preferred embodiment of the invention, the magnetic actuation field rotates during the times it is present. A rotation of the magnetic actuation field can induce a corresponding rotation of the magnetic particles, particularly of those particles that are agglomerated in clusters. As the clusters are typically anisotropic in shape, their rotation will affect their interaction with the (anisotropic) input light. The output light will therefore comprise modulations that depend on the rotation of the magnetic actuation field, which in turn allow conclusions about the magnetic particles or clusters they originate from.

The clusters of magnetic particles that are detected by the method and the sensor device may preferably be clusters formed by two magnetic particles. These two-particle clusters are practically important and have a pronounced anisotropy, which makes them apt for a detection in a (rotating) magnetic actuation field.

The sample may preferably comprise magnetic particles of two different kinds that can bind to a target component in the sample in a sandwich configuration. The sample may for example comprise magnetic particles coated with a first antibody and magnetic particles coated with a second antibody, wherein each of these antibodies can bind to a different epitope on a target molecule in the sample. The presence and/or amount of these target molecules is typically the value one is actually interested in. It can be determined via the detection of clusters formed by the aforementioned sandwich configuration of two magnetic particles of different kind coupled by a target molecule. The detected amount of such two-particle clusters is thus a measure for the amount of target component in a sample.

The output light may particularly comprise input light that was scattered by clusters of magnetic particles. Observing scattered light has the advantage that its amount (intensity) is proportional to the amount of scattering components. Small quantities of these components can therefore optimally be tackled with highly sensitive light detectors, because there is no high baseline signal that has to be dealt with. It should be noted that the output light often comprises light that was scattered by clusters of interest as well as by single magnetic particles or other agglomerates. To separately determine those components of output light that relate to clusters of interest, these clusters may be actuated in a particular way by the magnetic actuation field, which results in a corresponding characteristic modulation of their output light components.

The invention further relates to the use of the sensor device described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

In recent years, an increased demand for more pervasive and effective healthcare systems is affecting the world of in vitro diagnostics, putting the stress on the achievement of effective point-of-care solutions. The achievement of such goal is particularly demanding due to the requisites of point-of-care diagnosis: since the tests need to be performed at the patient location, they must be rapid, sensitive, quantitative and accurate. Moreover the platform on which the test is performed needs to be portable and easy-to-use.

Figure 1:
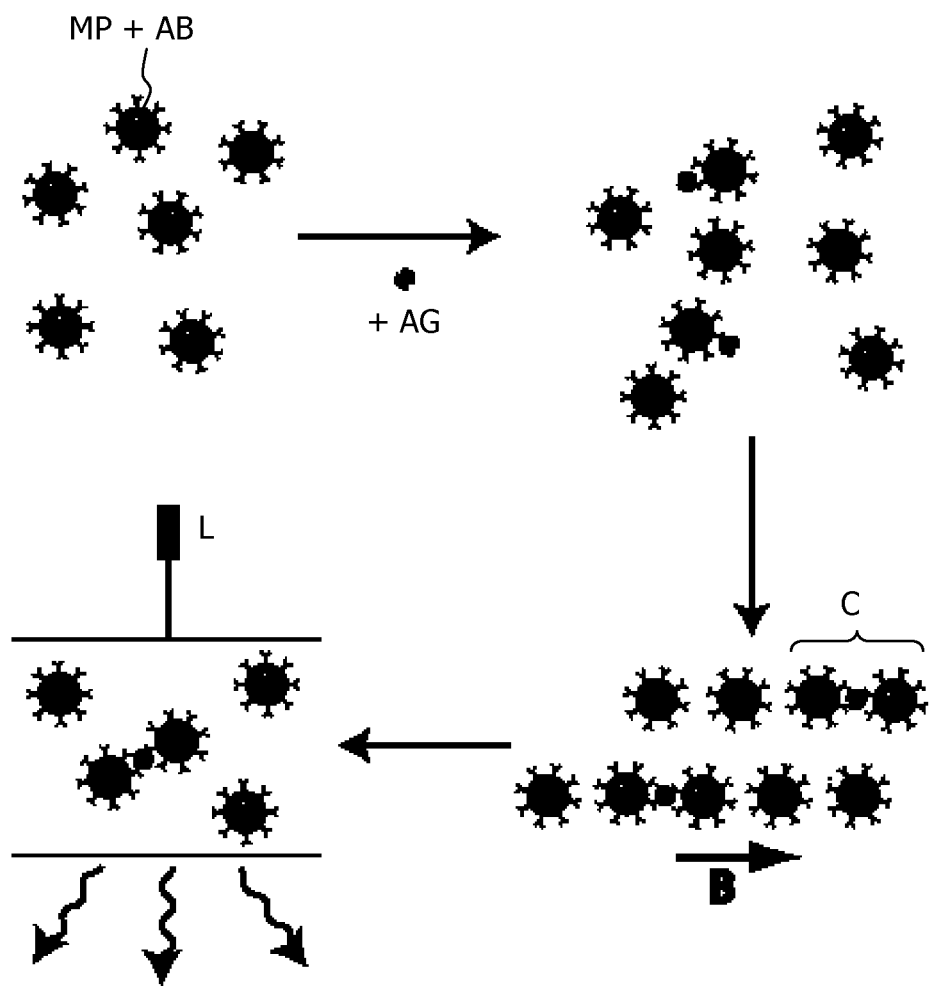
FIG. 1 schematically sketches events in a sample in which magnetic particles bind to a target molecule and form clusters.

Magnetic cluster assays provide a volumetric and surface-free architecture and therefore they are intrinsically rapid and cost-effective. FIG. 1 schematically sketches four consecutive steps of a typical magnetic cluster assay based on magnetic confinement of the magnetic nanoparticles MP to enable effective cluster formation.

As a first step (FIG. 1 top left), the magnetic particles MP coated with antibodies are provided. In a second step (FIG. 1 top right), the antigen AG is added and binds to magnetic particles. In a third step (FIG. 1 bottom right), the sample is exposed to a magnetic field B, causing the formation of particle chains or clusters C. In the last step (FIG. 1 bottom left), the sample is illuminated with a light source L, and the light scattered by the clusters is detected.

The literature describes the fact that magnetic chain formation is particularly powerful to enhance the kinetics of the particle-to-particle binding process, allowing for very rapid assays (Baudry et al., Proceedings of the National Academy of Sciences 2006, 103, (44), 16076.). The magnetic chain formation enables effective cluster formation by concentrating the magnetic particles and forcing them to remain in close contact between each other despite their repulsive nature.

A typical magnetic actuation protocol consists for example in applying a uniform magnetic field to a sample containing nanoparticles that have been incubated with the target biomolecule to detect. When the field is active, the nanoparticles arrange themselves into chains and are free to vibrate and rotate while in close proximity with each others. Consequently the specific bond can be effectively formed, as sketched in FIG. 1.

Figure 2:
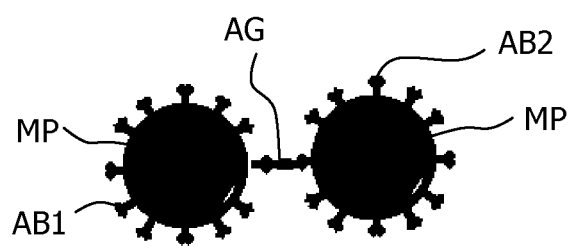
FIG. 2 is an enlarged picture of a sandwich configuration of two magnetic particles and one target molecule.

A particular situation arises when the magnetic nanoparticles MP are coated with different monoclonal antibodies AB1 and AB2, as illustrated in FIG. 2. The antibodies can specifically bind different sites of the antigen AG, thus forming a two-particle cluster with a sandwich configuration (FIG. 2).

In particular for the aforementioned assays, it is proposed here to use a "dynamic" actuation in terms of repeated pulses. As will be explained in more detail below, the application of repeated pulses can surprisingly reduce non-specific interactions and enhance the number of binding events.

The introduction of pulsed actuation in magnetic cluster assays serves a two-fold purpose. Primarily, the biomolecule to detect is caught by means of a sandwich configuration, in which monoclonal antibodies that specifically bind to different epitopes of the antigen are used (cf. FIG. 2). In order to maximize the number of specific bonds, during the magnetic actuation phase the number of collisions needs to be maximized, so that the a large number of random encounters makes more favorable the probability that particles coated with complementary antibodies can meet and effectively interact with the antigen.

A second relevant aspect relates to the fact that when superparamagnetic particles are dispersed in aqueous solutions they retain a small negative charge that helps to keep them separated and avoid non-specific clustering. The use of magnetism to stir the particles allows them to overcome the electrostatic repulsion and they are forced to remain in close proximity of each other; this is beneficial for speeding up the kinetics of cluster formation, however it also introduces a not negligible amount of non-specific interactions. Consequently, the use of magnetism needs to be carefully evaluated and balanced to optimize the generation of specific clusters and to minimize the number of non-specific clusters.

Figure 3:
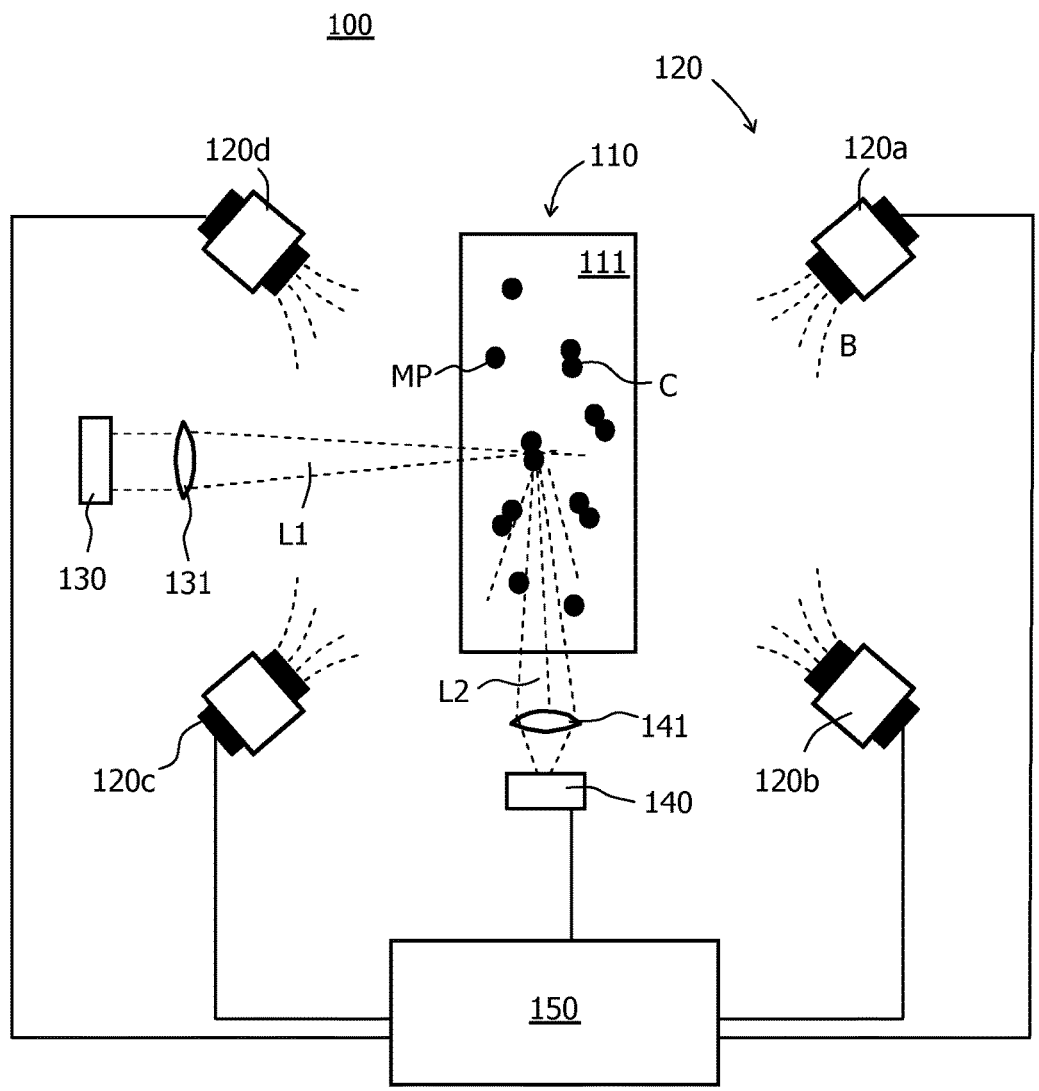
FIG. 3 schematically sketches a sensor device according to the present invention.

The approach proposed by the present invention can be implemented in a sensor device 100 (optomagnetic platform) as sketched in FIG. 3. This sensor device 100 comprises a sample container or cartridge 110 with a sample volume 111 in which a sample fluid with magnetic particles or beads MP can be provided. In the shown example, the sample cartridge 110 is a glass tube of square cross section.

The sensor device 100 further comprises a reader, of which only the most relevant components are schematically sketched. These components comprise:

- A magnetic field generator 120, which in the shown example consists of four electromagnets 120a, 120b, 120c, 120d. These magnets are arranged at the corners of a rectangle or square and are aligned with their axes towards some centre within the sample volume 111. By an appropriate sequential control of the currents in the electromagnets, a uniform rotating magnetic field B can be generated within the sample volume.
- A light source, for example a laser diode 130 or an LED, which emits a collimated (laser) beam of input light L1 that is focused by a lens 131 into the sample volume 111.
- A light detector 140, for example a photodiode or an image sensor. Output light L2 coming from the sample volume 111 is focused by means of a thin lens 141 onto the active surface of the light detector. The output light L2 consists in the shown embodiment of input light L1 that was scattered by components of the sample volume, particularly by magnetic particles MP and/or clusters C of these particles.
- A control unit 150 that is coupled to the magnetic field generator 120 and to the light detector 140 in order to control them and to process the measurement signals provided by the light detector 140.

When the described sensor device operates, the magnetic field generator 120 generates a rotating magnetic field B that induces a corresponding rotation of the clusters C of magnetic particles. While rotating, these clusters C expose a time-dependent cross-section to the incoming light L1, therefore introducing a modulation of the light intensity L2 scattered by the sample. Such modulation is mostly at twice the frequency of rotation of the clusters, since they are symmetric and their cross-section is the same after a rotation of 180°. A Fast Fourier Transform (FFT) algorithm can be applied to the recorded signal, and the amplitude of the FFT at twice the frequency of the magnetic field can be defined as signal S that indicates the amount of clusters of interest.

To prove the described concept, experiments were made with 500 nm magnetic particles MP, coated with antibody against epitopes 10 and 66 of prostate specific antigen (PSA). The actuation scheme adopted consisted in applying uniform rotating magnetic field pulses of 25 mT for 2 s for 20 times. Moreover, variable "pauses" with no field present between the shooting of consequent pulses were applied. For a duration of the pauses of 0 s, the actuation is "continuous" in the sense that a uniform rotating field rotating at 1 Hz is applied for the full duration of the actuation protocol.

Figure 4:
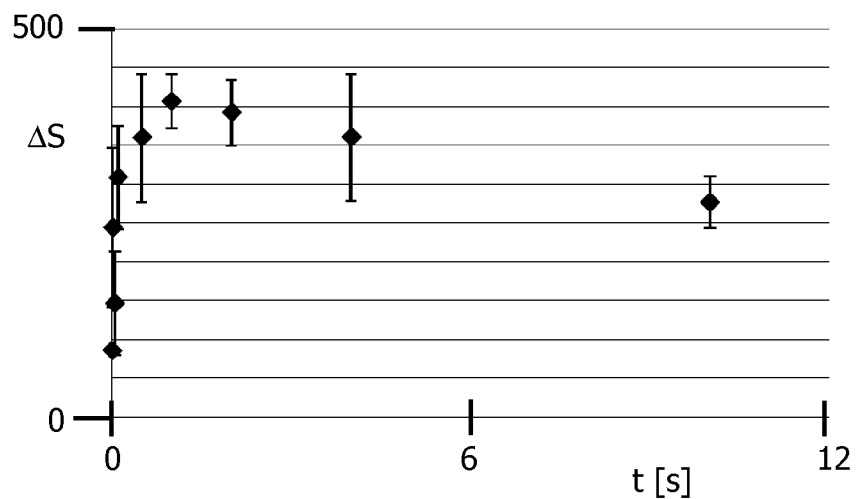
FIG. 4 is a diagram representing the difference of output signals (vertical axis) in dependence on the duration of pauses (horizontal axis) in the magnetic actuation field.

FIG. 4 reports the difference in signal, $\Delta S$, between the average signal (over three independent measurements) at a PSA concentration of 100 pM and the average signal (over three independent measurements) at 0 pM in dependence on the duration d of the pauses (horizontal axis). It is clearly visible that there is an improvement of the specific signal of almost a factor 3 introducing pulsed actuation.

The experiment further shows that there is an optimum of the specific signal with respect to the pause-duration d (which is dependent on the actual particle concentration and on the magnetic properties of the particles). In the shown example, this optimum lies at about 1 s. Experiments like this can therefore be used as a calibration procedure to find optimal operation parameters of the magnetic actuation.

Figure 5:
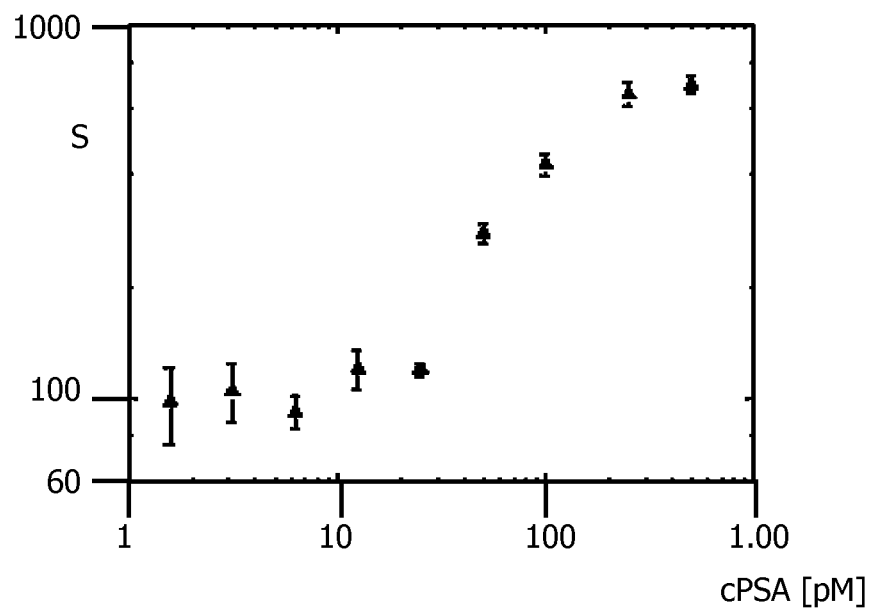
FIG. 5 is a diagram showing the output signal (vertical axis) in dependence on the concentration of a target component (horizontal axis).

The use of pulsed actuation and the consequent increase in signal is also fundamental in order to achieve a reproducible and sensitive assay. This is illustrated with respect to FIG. 5, which shows a dose-response curve for a PSA assay based on pulsed actuation. The (preliminary) experiments demonstrate a limit of detection of almost 10 pM.

To prove that pulsed actuation can be beneficial for reducing the amount of non-specific interactions, a further experiment was performed where the signal before and after magnetic actuation was measured for a sample containing 0 pM of PSA. In the case of continuous actuation an increase in the amount of clustering close to a factor 3.5 was registered, whereas while making use of pulsed actuation, the increase in signal was below a factor 2.

The aforementioned experiment has been performed by applying the following sequence of pulses: a magnetic field of 3.5 mT of amplitude was applied for 2 s, then for a pause of 4 s the amplitude of the field was zero. The particle concentration used was 0.1 mg/ml of 500 nm magnetic particles (AdemTech).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for detection of clusters (C) of magnetic particles (MP) bound to target molecules, respectively, in a sample volume, the method comprising:
   irradiating the sample volume with input light (L1);
   actuating the magnetic particles in the sample volume by exposing the sample volume to a rotating magnetic actuation field (B) to form said clusters rotating in the magnetic actuation field, such that the sample volume comprises bound magnetic particles and unbound magnetic particles, wherein said magnetic actuation field is interrupted by at least one pause; and
   detecting output light (L2) during the actuation of the magnetic particles, the output light originating from an interaction of the input light (L1) with the clusters (C) of magnetic particles (MP) in the sample volume, wherein intensity of said output light is modulated by the rotation of said clusters in said rotating magnetic actuation field;
   wherein a duration of the at least one pause ranges between about 0.1 s and about 10 s.

2. The method according to claim 1, wherein the duration of the at least one pause and/or a number of pauses is experimentally determined.

3. The method according to claim 1, wherein the duration of the at least one pause ranges between about 1 s and about 2 s.

4. The method according to claim 1, wherein the magnetic actuation field (B) is interrupted by about 10 to about 50 pauses.

5. The method according to claim 1, wherein each of the detected clusters (C) is formed by two magnetic particles (MP) bound to one of the target molecules.

6. The method according to claim 1, wherein the sample volume comprises magnetic particles (MP) of two kinds able to bind to a target molecule in the sample volume in a sandwich configuration.

7. The method according to claim 1, wherein the output light (L2) comprises input light (L1) which was scattered by the clusters (C) of magnetic particles in the sample volume.

8. The method according to claim 1, further comprising:
   detecting an amount of clusters in the sample volume based on the modulated intensity of the output light.

9. The method according to claim 8, further comprising:
   determining an amount of the target molecules in the sample volume based on the detected amount of clusters.

10. A method of determining an amount of target molecules in a sample, the method comprising:
    providing magnetic particles coated with antibodies in the sample;
    exposing the sample to a magnetic field, causing formation of clusters comprising at least two magnetic particles bound to a target molecule via the antibodies;
    rotating the magnetic field, causing rotation of the clusters in the sample, wherein said magnetic field is interrupted by at least one pause;
    irradiating the sample with input light;
    detecting output light during rotation of the magnetic field, the output light originating from an interaction of the input light with the clusters, wherein intensity of the output light is modulated by the rotation of the clusters in the rotating magnetic field; and
    determining an amount of the target molecules in the sample based on an amount of clusters detected using the modulated intensity of the output light.

11. The method of claim 10, wherein the at least two magnetic particles bound to each of the target molecules form a sandwich configuration, comprising two magnetic particles of different kinds coupled by the target molecule.

12. The method of claim 10, wherein a duration of the at least one pause ranges between about 0.1 s and about 10 s.

* * * * *